United States Patent [19]

Warden et al.

[11] 4,259,071

[45] Mar. 31, 1981

[54] DENTAL POLISHING CUP FOR USE WITH A ROTARY DENTAL HAND PIECE

[76] Inventors: Fuller Warden, 1231 E. 30th Pl., Tulsa, Okla. 74114; Eugene W. Lewis, 5415 S. 68 E. Pl., Tulsa, Okla. 74145

[21] Appl. No.: 61,765

[22] Filed: Jul. 30, 1979

[51] Int. Cl.³ .............................................. A61C 3/06
[52] U.S. Cl. .................................................. 433/166
[58] Field of Search ................. 433/146, 125; 51/394, 51/395, 358, 359, 356, 266, 267

[56] References Cited

U.S. PATENT DOCUMENTS

| 441,524 | 11/1890 | Whitcomb | 433/166 |
| 2,738,528 | 3/1956 | Fridge, Sr. | 433/166 |
| 3,621,577 | 11/1971 | Spinello | 433/166 |

Primary Examiner—Robert Peshock
Attorney, Agent, or Firm—James H. Chafin

[57] ABSTRACT

A dental polishing cup for use with a rotary dental hand piece. The cup has a truncated conical shaped body member with a similar truncated conical shaped cavity in the large open end thereof, the opposite smaller end of the cup being attachable to the rotary hand piece. The inside wall of the cavity is provided with spiral ridges or grooves, the direction of the spiral being such that when the cup containing polishing compound is pressed against the teeth and rotated, the spirals will tend to force the compound inwardly toward the center of the cup.

7 Claims, 6 Drawing Figures

DENTAL POLISHING CUP FOR USE WITH A ROTARY DENTAL HAND PIECE

BACKGROUND OF THE INVENTION

1. Field of the Invention

The present invention relates to dental polishing cups and more particularly, but not by way of limitation, to a cup having spiral ridges or grooves designed to tend to force the polishing compound inwardly toward the center thereof.

2. History of the Prior Art

For many years, dentists have been using various sized and shaped rubber cups for rotatingly applying polishing compound to teeth as a part of the typical teeth cleaning operation to remove plaque and stain build up.

The cups are generally of a truncated conical shape or a bell shape having an open cavity portion in the larger end of the cup.

Many of the cups presently in use have vanes or protrusions within the cavity thereof in an attempt to effect greater surface area contact between the cup and the tooth being polished for more efficient cleaning and polishing.

When the cup is pressed into contact with the teeth, the flexibility of the outer skirt of the cup causes the cup to flare out and flatten against the teeth and when rotated a large portion of the polishing compound that has been placed inside the cup spins outwardly away from the cup and is lost without ever having served its function as an abrasive compound on the outer surface of the tooth.

The waste of the material due to the loss of this compound is not nearly so significant as the loss in time since the cup quickly runs out of the polishing compound and must be refilled again.

There have been attempts to provide devices for the polishing of teeth wherein the compound is fed through an introduction port in the center of the cup into the cavity of the cup. While this prevents the loss of time in having to refill the cup constantly, it does not prevent the waste of material and causes the cartridge carrying the supply of the compound to have to be rather large and bulky.

Hence, the cups that are presently on the market, while possibly being efficient in the cleaning process itself are grossly inefficient in the use of the cleaning and polishing compound.

SUMMARY OF THE INVENTION

The present invention provides a polishing cup for use with a dental rotating hand piece which, while maintaining the outward appearance of the prior art cups presently available, contains spiral guide elements which are designed to tend to force the polishing compound inwardly toward the center and upwardly into the cavity of the cup while still maintaining a large surface polishing area. These spiral guide elements may be in the form of inwardly extending spiral ridges on the inside wall of the cavity or spiral grooves on the inside wall of the cavity. The spiral elements extend from the inner end of the cavity, around the wall of the cavity in the direction of intended rotation of the cup, to the lower or large end of the cup.

Hence, when the cup is placed into pressing contact with the teeth, it will flare out and tend to flatten against the teeth and when rotation is effected, the spiral elements will tend to force the polishing compound back toward the center of the cup and upwardly into the cavity thereby holding the compound in contact between the cup and the teeth long enough to fully utilize the abrasive action thereof.

DESCRIPTION OF THE DRAWINGS

Other and further advantageous features of the present invention will hereinafter more fully appear in connection with a detailed description of the drawings in which.

DESCRIPTION OF THE PREFERRED EMBODIMENTS

Figure 1:
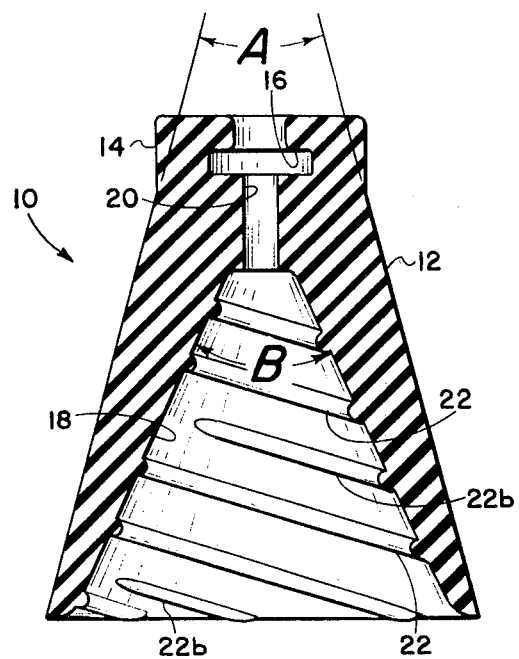
FIG. 1 is an elevational sectional view of a dental polishing cup embodying the present invention.

Referring to the drawings in detail, reference character 10 generally indicates a dental polishing cup which comprises a substantially truncated conical shaped body portion 12 which is typically made of some flexible material such as rubber or some rubber compound which has elastic properties.

The outside surface of the truncated conical shaped body portion is constructed to have an included angle A. The upper or smaller end of the body member 12 is provided with a cylindrical portion 14 having a centrally disposed flanged recess 16 which is for the primary purpose of mounting the polishing cup 10 to a suitable dental handpiece such as a doriot or even a portable rotary handpiece, (not shown).

Within the body member 12 is a centrally disposed truncated conical shaped cavity 18 which is open at the bottom end or the larger end of the body member 12. The included angle of such cavity member is represented by reference character B which is typically larger than the included angle A of the body member whereby the upper portion of the wall between the cavity and the outside surface of the body member is thicker than it is at the lower larger end.

When the dental polishing cup 10 is to be used with a device that feeds paste or polishing compound through the center of the cup, the cup is equipped with a central longitudinal bore or port 20 which provides open communication between the top or smaller end of the body member 12 and the interior of the cavity 18.

Figure 2:
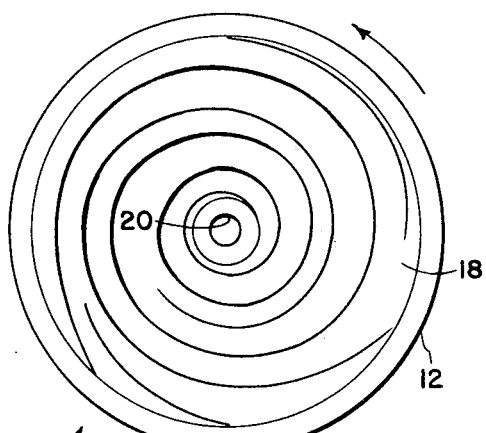
FIG. 2 is a bottom view of the cup of FIG. 1.

The wall of the cavity 18 is then provided with a plurality of spiral ridges 22, some of the ridges starting at the top or smallest most portion of the cavity wall and extending around the cavity wall downwardly toward the open end in a direction which is the same direction as the direction of rotation of the cup 10 as more clearly is shown in FIG. 2 which is a bottom of the cup of FIG. 1.

Figure 3:
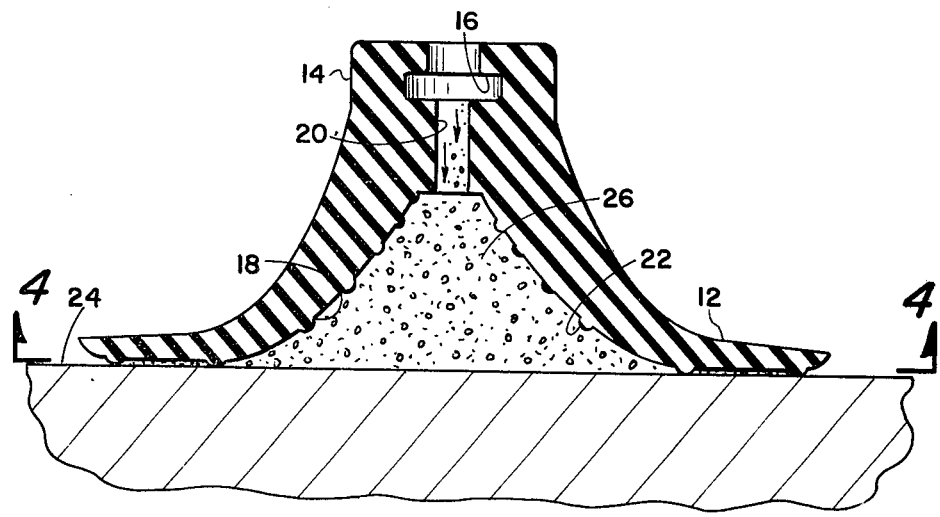
FIG. 3 is an elevational sectional view of the cup of FIG. 1 being in pressing contact against the surface of a tooth.

Typically when the cup is put into use, paste is either extruded through the port 20 into the cavity 18 of the cup or in the case where there is no port 20, paste is simply dipped or applied to the interior of the cup and the cup is then pressed against the surface of the tooth or other object to be polished, the tooth being represented in FIG. 3 by reference character 24. When the cup is pressed into contact with the surface of the tooth 24, the sidewalls of the cup or the body portion 12 flares outwardly which brings more surface of the cavity wall 18 into contact with the surface of the tooth with the polishing compound being somewhat trapped in between.

As hereinbefore stated one of the problems with prior art devices is that when the cup is made to rotate the centrifugal force applied to the paste compound and the pressing operation causes much of the paste to be lost in the polishing process without being fully used.

Figure 4:
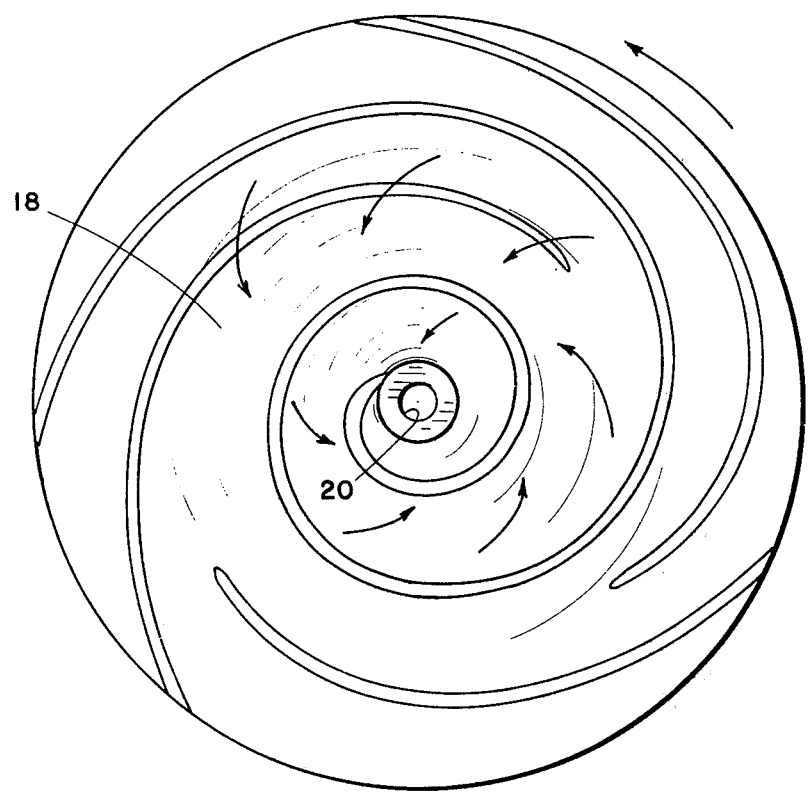
FIG. 4 is a sectional bottom view of the cup of FIG. 3 and taken along the broken line 4—4 of FIG. 3.

Referring to FIGS. 3 and 4, FIG. 4 is a bottom view of the cup in its flared position in contact with the tooth wherein paste or polishing compound is between the cup and the tooth. The polishing compound is indicated by reference character 26.

When the cup is set into rotation in the direction shown by the arrow 28, the paste trapped therein will start its abrasive action on the tooth and the centrifugal force caused by the rotation of the paste will tend to make it want to move outwardly. However, as a particle of paste moves outwardly along the surface of the cup, it will encounter one of the ridges 22 which will tend, due to its spiral shape, to force the paste back toward the center of the cup so that it will be fully utilized before finally being expelled around the outer periphery of the cup.

It is not known for certain but it is felt that there will be an accumulation of paste along the inside edges of the ridges 22, the major part of this accumulation being constantly forced toward the center as the cup is rotated.

It can be seen from FIG. 3 that a large portion of the interior of the cup (the cavity) is still in the form of a cavity after the bottom portion of the cup is flared outwardly. The ridges will still react with the paste 26 to tend to force it upwardly within the cavity.

Figure 5:
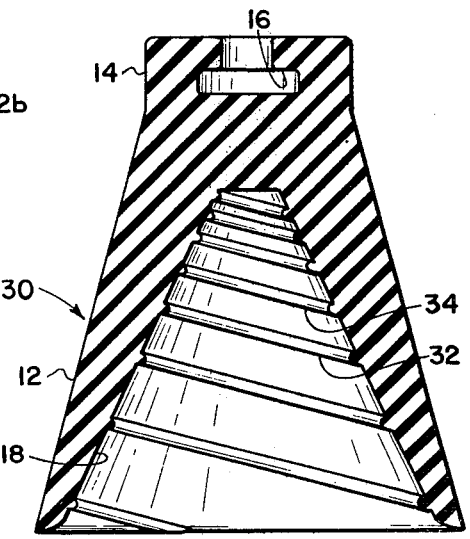
FIG. 5 is a sectional elevational view of a cup having a plurality of parallel spiral elements.

Referring now to FIG. 5, reference character 30 generally indicates a cup which is similar to the construction of the cup 10 having a body member 12 and a cavity 18 but wherein the inside surface of the cavity is provided with a different spiral pattern of ridges, one ridge being identified by reference character 32 and a second spiral ridge identified by reference character 34. The ridges 32 and 34 constitute mutual parallel spirals, the corresponding element of each spiral being parallel to each other. On the other hand, the spirals 22 of the cup 10 constitute one long continuous spiral and a plurality of partial spiral ridges 22b.

Figure 6:
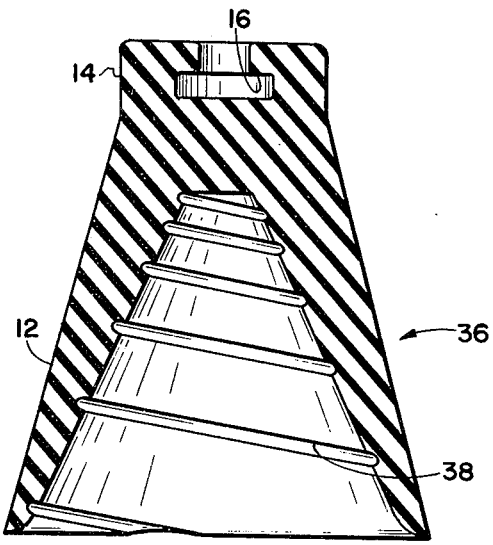
FIG. 6 is an elevational sectional view of a cup having grooves instead of ridges.

Referring now to FIG. 6, reference character 36 generally indicates a polishing wherein the spiral guide elements inside the cup are grooves 38 as opposed to ridges provided in the cups hereinbefore described.

It is further pointed out herein that where the cup has been described as having the overall outside shape of a truncated cone, departures from this shape may be made within the scope of the invention such as curved bell shapes and the like which is true also of the cavity 18 whithin the cup. Therefore, wherever the term "substantially truncated conical shape" is used in this application it would also apply to reasonable deviations from that shape.

Whereas, the present invention has been described in particular relation to the drawings attached hereto, other modifications apart from those or suggested herein may be made within the spirit and scope of the invention.

What is claimed is:

1. A polishing cup for cleaning and polishing teeth for use with a rotary hand piece and a dental cleaning polishing compound, the cup comprising; a substantially truncated conical shaped body member of flexible elastic material, attachment means provided at a first small end thereof, a substantially truncated conical shaped cavity within the second large end of the cup for containing cleaning and polishing compound therein, and at least one spiral guide means around the peripheral wall of the cavity, each spiral guide means extending from within the cavity outwardly around the wall of the cavity in the direction of intended rotation of the cup for coacting with the teeth to force the polishing compound inwardly toward the center of and upwardly within the cavity within the cup.

2. A polishing cup as set forth in claim 1 wherein the spiral guide means comprises at least one inwardly extending spiral ridge.

3. A polishing cup as set forth in claim 1 wherein the cavity has an included angle greater than the included angle of the body member.

4. A polishing cup as set forth in claim 2 wherein there is a plurality of inwardly extending spiral ridges which are mutually parallel.

5. A polishing cup as set forth in claim 1 and including a central longitudinal bore through the cup from the first end of the body member into open communication with the cavity therein.

6. A polishing cup as set forth in claim 1 wherein the spiral guide means comprises at least one spiral groove.

7. A polishing cup as set forth in claim 5 wherein there is a plurality of spiral grooves which are mutually parallel.

* * * * *